(12) United States Patent
Morton

(10) Patent No.: US 7,364,561 B1
(45) Date of Patent: Apr. 29, 2008

(54) ANKLE BRACE WITH REMOVABLE PLATE

(75) Inventor: Scott T. Morton, New Albany, IN (US)

(73) Assignee: Active Ankle Systems, Inc., Jeffersonville, IN (US)

( * ) Notice: Subject to any disclaimer, the term of this patent is extended or adjusted under 35 U.S.C. 154(b) by 227 days.

(21) Appl. No.: 11/236,030

(22) Filed: Sep. 27, 2005

(51) Int. Cl.
*A61F 5/00* (2006.01)
(52) U.S. Cl. ............................ 602/23; 602/27; 128/882
(58) Field of Classification Search ................. 602/5, 602/16, 23, 26–27; 128/882
See application file for complete search history.

(56) References Cited

U.S. PATENT DOCUMENTS

| | | | |
|---|---|---|---|
| 5,094,232 A * | 3/1992 | Harris et al. .................. | 602/16 |
| 5,676,642 A * | 10/1997 | Peters ........................... | 602/27 |
| 6,117,098 A * | 9/2000 | Weber et al. .................. | 602/27 |
| 6,146,350 A | 11/2000 | Morton | |
| 6,656,145 B1 | 12/2003 | Morton | |
| 7,192,408 B2 * | 3/2007 | Win ............................. | 602/16 |

\* cited by examiner

*Primary Examiner*—Michael A. Brown
(74) *Attorney, Agent, or Firm*—James E. Cole; Middleton Reutlinger

(57) ABSTRACT

An ankle brace with a removable plate comprising a stirrup having a bottom portion and an inner and outer upright leg depending upward therefrom. An inner pivot leg is pivotally attached to an upper end of the inner upright leg of the stirrup and an outer pivot leg is pivotally attached to an upper end of the outer upright leg of the stirrup. An exterior plate is removeably attached to an outer side of the outer pivot leg.

14 Claims, 5 Drawing Sheets

ANKLE BRACE WITH REMOVABLE PLATE

BACKGROUND OF THE INVENTION

1. Field of Invention

The present invention relates to orthopedic devices and in particular ankle braces.

2. Description of the Related Art

Ankle injuries are among the most common injuries in sports. In order to protect the ankle, many athletes have wrapped the ankle area with adhesive tape. The application of tape is expensive both because it is time consuming and because of the tape itself. It is also not very effective because the tape loosens quickly after exercise has begun. The use of exercise tape has also been shown to weaken ankles if used over a long period of time because it causes a loss of plantarflexion and dorsiflexion.

When an ankle is injured, the traditional method for promoting healing is to apply pressure to the area to reduce swelling and to prevent lateral movement of the ankle. The method of applying pressure to the ankle limits the range of motion over the ankle. When large areas are covered by a compression device, the material in contact with the foot must be fairly flexible or soft, such as an elastic bandage or an air bag, in order to avoid discomfort to the wearer and provide the amount of flexibility and movement required for athletic flexing of the ankle joint. This severely limits the amount of pressure that can be applied to the injury site in order to reduce the swelling caused by the ankle injury. An additional drawback found when air bag type devices are utilized is that the ankle and foot directly contact the bag in order to move, causing irritation of the skin. This irritation may be caused from the friction incurred by such contact which, in turn generates heat which is not desirable to add to a swollen area of the body.

Another treatment method is to exercise the joint to promote healing. Exercise brings greater blood flow to the area and prevents the atrophy of the muscles involved.

The current trend in medicine is to promote exercise as soon as possible. However, in traditional treatment methods, the ankle could not be properly exercised until after the compression device was removed thereby greatly delaying the exercise therapy. It is therefore desirable to provide an orthopedic device which allows exercise of the injury site while additionally resisting mobility in the direction which would irritate the injury.

As indicated, one method to promote healing of the ankle is preventing lateral movement of the ankle thereby allowing forward and backward flexing but preventing inward and outward flexing. The wearing of an ankle brace provides such protection while preventing inflammation of the injured ankle areas. Visually this forward and backward flexing is based upon a brace which is hinged in such a way to pivot backwards and forwards.

Most prior art devices that provide for pivoting of the ankle in addition to providing lateral support thereof do not provide a means for adjusting the stiffness of the lateral support, modifying the appearance of the brace, nor the capability of displaying a logo or insignia thereon.

SUMMARY OF THE INVENTION

The present invention provides an ankle brace which pivots along the same axis as the ankle and which has an easily removable, interchangeable, non-permanent exterior plate.

The ankle brace of the present invention incorporates an ankle brace having an exterior plate. More particularly, the present invention includes an ankle brace to be worn by a wearer to prevent ankle injury or encourage healing of an injured ankle and provide adjustability in lateral support as well as a means for displaying a team color or other insignia.

The present invention is to provide axial movement or flexing of the ankle forward and backwards while additionally providing lateral support in order to prevent inversion or eversion of the ankle. The ankle brace has a heel stirrup with a flat base portion which is pivotally connected to an inner and outer pivot leg in combination with an adjustable strap positioning fastener for protecting and exercising an injured ankle. The present invention has a stirrup portion which is pivotally connected to inner and outer pivot legs, the pivot legs have on the interior thereof softening pads for compression directly against the wearer's leg or ankle. Additionally, a connecting strap is provided for tightening the inner and outer pivot legs in combination with the softening pads directly against the leg. A removable plate attachment means is provided on the exterior surface of the outer pivot leg. A removable plate is attached to the exterior surface of the outer pivot leg providing additional support and/or a means for displaying a logo, team color, or other insignia. The removable plate may be placed under the connecting strap providing additional support or over the connecting strap providing more display area.

The hinge connection between the inner and outer legs of the stirrup and the inner and outer pivot legs may be a single piece hinge. The adjustable strap or straps have a retaining means such as a hook and loop fastener at distal ends to firmly attach the pivoting legs of the ankle brace to the wearer. The connecting strap(s) may pass over or under the removable plate on the outer pivot leg. On the interior of the inner and outer pivot leg is attached softening pads which are secured to the pivot legs by a hook and loop fastener such as Velcro™ or other attachment means known by a person of ordinary skill in the art.

DETAILED DESCRIPTION OF THE PREFERRED EMBODIMENTS

Figure 1:
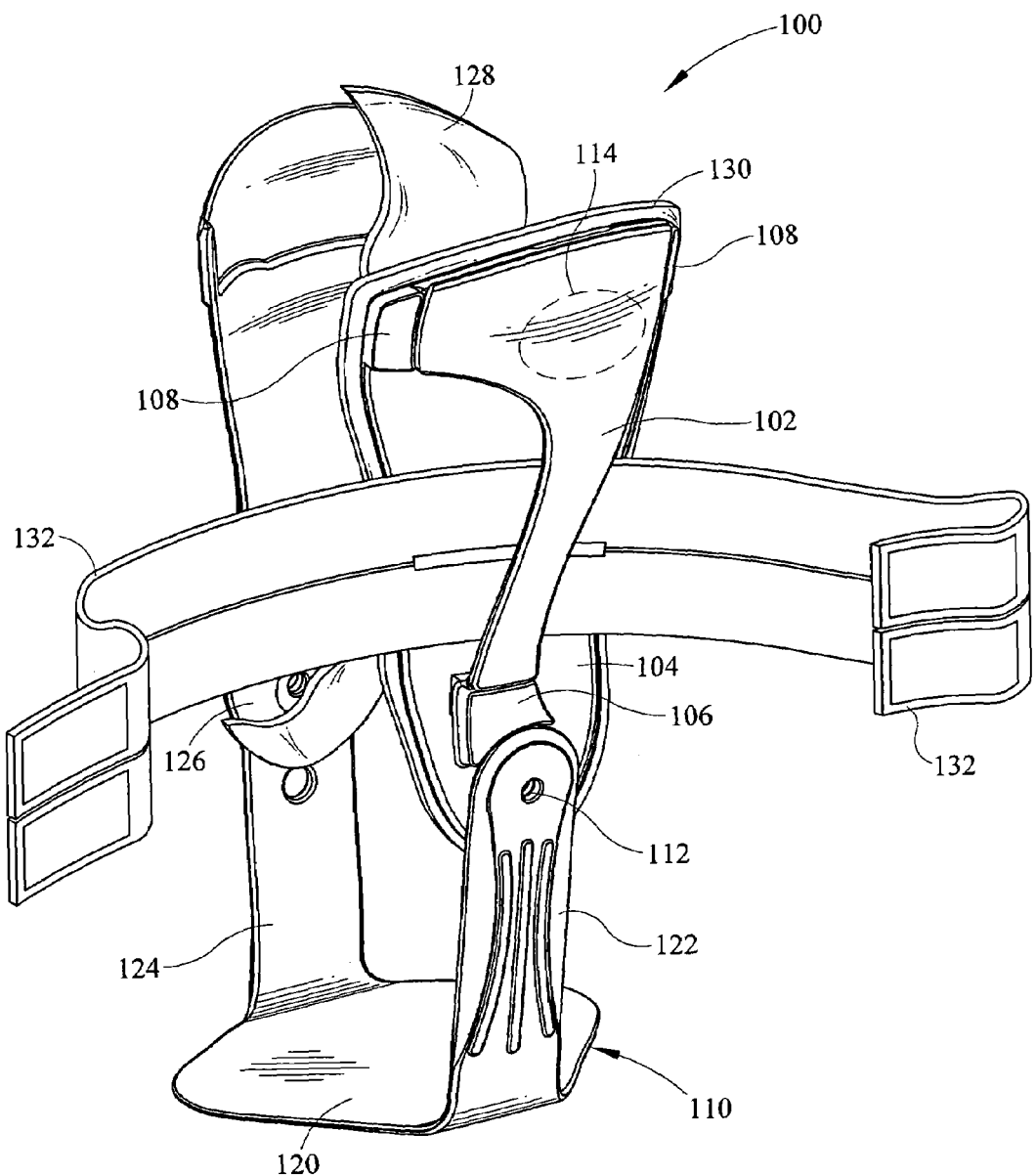
FIG. 1 is a perspective partial cut-away view of an embodiment of an ankle brace having a removable plate on the outer side of retaining straps.

An embodiment of an ankle brace 100 of the present invention is shown in FIG. 1. In this figure, the stirrup 110 of ankle brace 100 is shown as being comprised of a substantially flat base portion 120, an inner upright leg 124 and an outer upright leg 122. Pivotally attached to the inner and outer upright legs 124 and 122 of stirrup 110 are outer pivot leg 104 and inner pivot leg 126. Such pivotal or rotatable connection to the stirrup 110 allows the inner and outer pivot legs 126 and 104 to move forward and backwards rotating about pivot point 112 while additionally providing lateral support through upright legs 126 and 104. Attached to the interior of the inner and outer pivot legs 126 and 104 are inner and outer softening pads 128 and 130 which contact directly against the wearer's leg. Wrapped around the exterior of the inner and outer pivot legs 126 and 104 is connecting strap or straps 132 which enables ankle brace 100 to be securely fastened around the wearer's leg. The inner and outer pivot legs 126 and 104 may be hingedly detachable from stirrup 110 while at the same time providing lateral support to the ankle through legs 126 and 104. Exterior plate 102 in the embodiment shown here removeably attaches within raised slots 108 and 106 to outer pivot leg 104 and has strap(s) 132 passing between outer pivot leg 104 and plate 102. In this configuration or embodiment, a display, logo, team color, or insignia may be displayed on the outer surface of ankle brace 100 with removable plate 102 without having a portion covered by strap(s) 132. Also shown here is a potential insignia or logo display area 114.

The stirrup 110 of the present invention is in a substantially "U" shape and is comprised of the substantially flat bottom portion 120 and the inner and outer upright legs 124 and 122. Both inner and outer upright legs 124 and 122 append substantially vertically from base portion 120. The stirrup 110 may be comprised of a strong thermoplastic material strong enough to prevent lateral shifting of the ankle retained between the inner and outer upright legs 124 and 122. The upright legs 124 and 122 may also be slightly offset to compensate for the typical slight outward pronation of the wearer's ankle.

Figure 2:
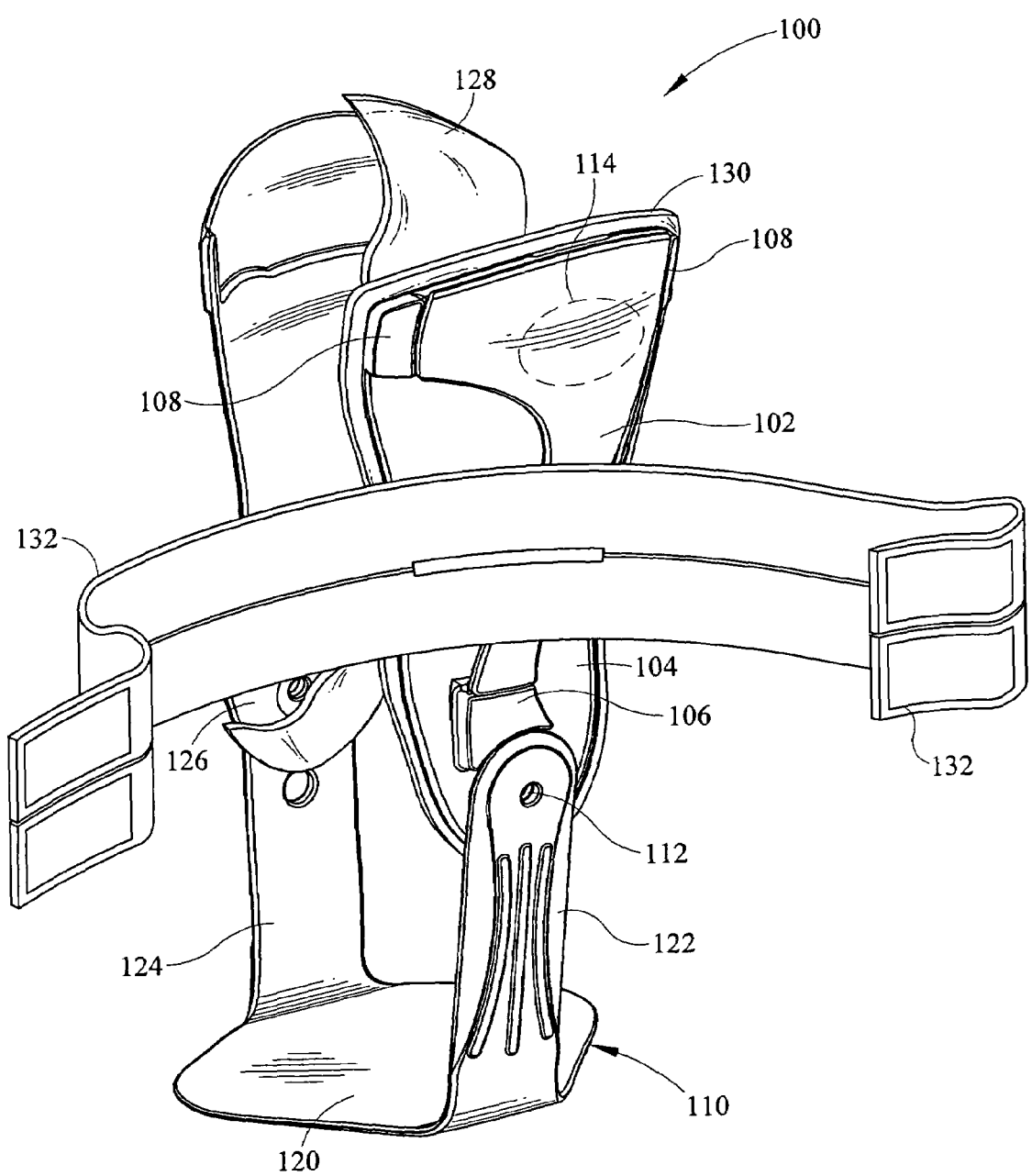
FIG. 2 is a perspective partial cut-away view of an embodiment of an ankle brace having a removable plate on the inner side of retaining straps.

FIG. 2 shows an embodiment of the ankle brace of FIG. 1 having connecting strap or straps 132 passing around the outside surface of exterior plate 102. Exterior plate 102 removeably connects to raised slots 108 and 106 where it provides a display area and a degree of increased lateral support. Having strap(s) 132 tightened around the outer side of exterior plate 102 and join around the ankle on the outside if inner pivot leg 126 further increases the lateral support offered by ankle brace 100.

Figure 3:
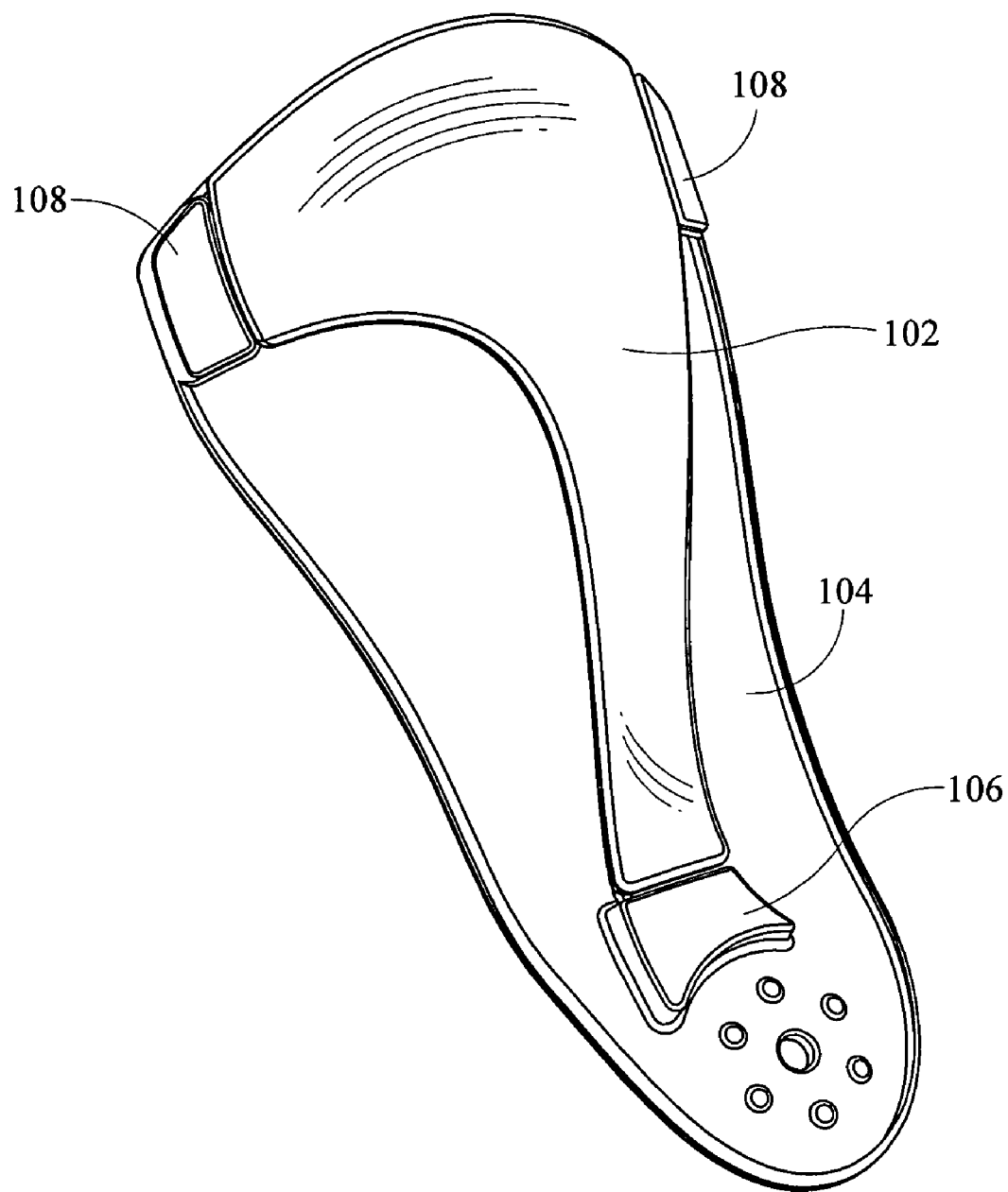
FIG. 3 is a perspective view of an embodiment of the outer pivot leg of the ankle brace of FIG. 1 having a removable plate attached thereto.

FIG. 3 shows outside pivot leg 104 having an embodiment of exterior plate 102 removeably attached thereto. In the embodiment shown, exterior plate 102 is in the form of a "T" having rounded side edges and a top contoured as the top of outside pivot leg 104. The top of exterior plate 102 is removeably attached to outside pivot leg 104 with tabs extending into raised slots 108. The bottom of exterior plate 102 is removeably attached to outside pivot leg 104 with a tab extending into raised slot 106.

Figure 4:
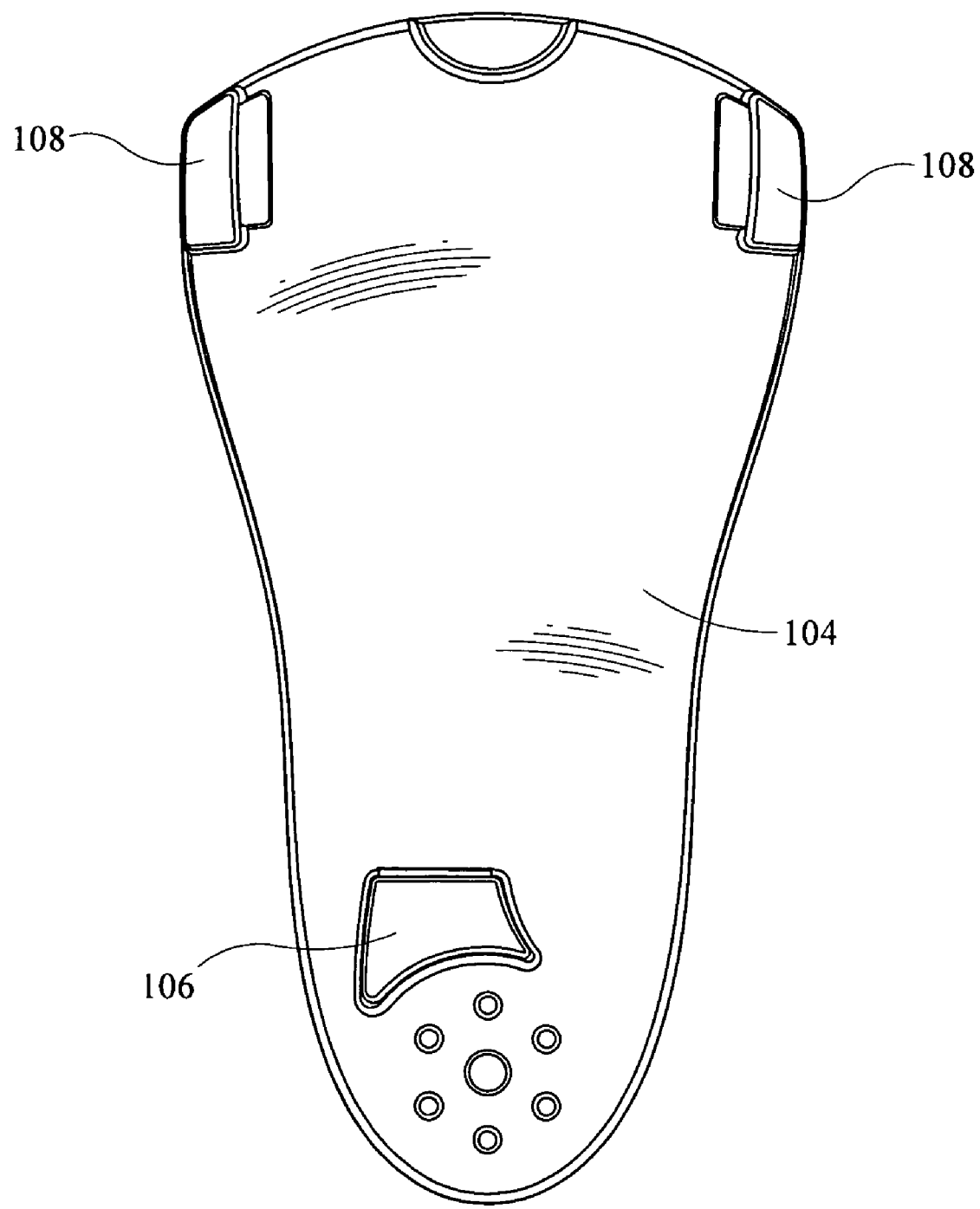
FIG. 4 is a front view of an embodiment of the outer pivot leg of the ankle brace of FIG. 1 showing an embodiment of a plate attachment means.

FIG. 4 shows an embodiment of outside pivot leg 104 having raised slots 108 in a horizontal configuration and raised slot 106 is in a vertical configuration. Such a configuration of raised slots 106 and 108 provides a means to removeably attach the embodiment of exterior plate 102 shown in FIGS. 1-3 and 5. However, it is to be understood that raised slots 108 and 106 may have a multitude of configurations which is only limited by the embodiments of exterior plate 102 that are to be attached thereto. For example, raised slots 108 may be in a vertical configuration for holding an embodiment of exterior plate 102 having vertically extending top tabs. Such a configuration would increase the additional lateral support offered by exterior plate 102. Other attachment means known by persons having ordinary skill in the art may be used to removeably secure exterior plate 102 to outer pivot leg 104. For instance, snaps, hook and loop fasteners, or other fasteners may be used in any configuration that holds exterior plate 102 to outer pivot leg 104 during exercise and provides any additional support that may be desired, if any.

Figure 5:
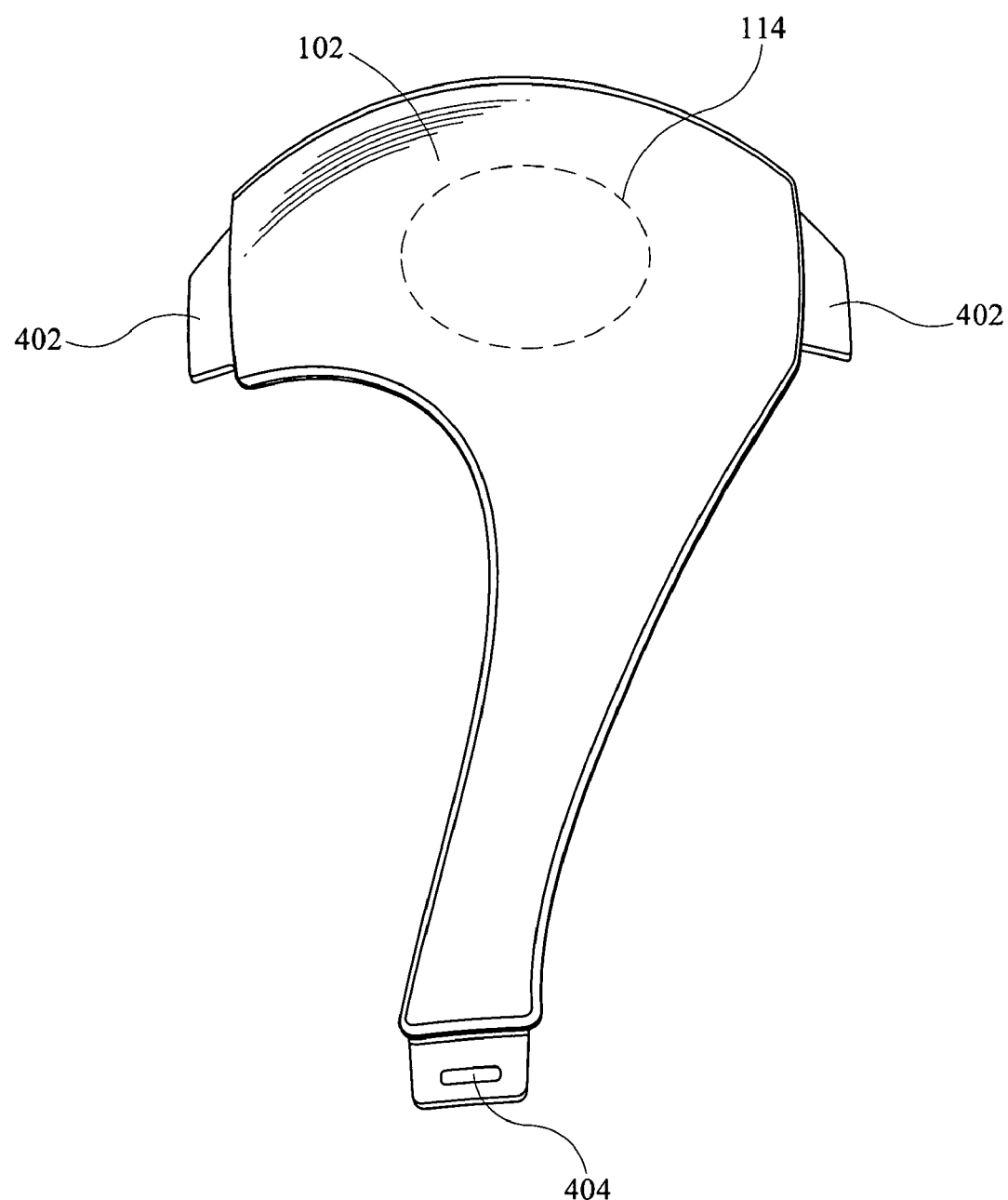
FIG. 5 is a front view of an embodiment of the removable plate shown in FIG. 1.

FIG. 5 shows an embodiment of exterior plate 102 in the form of a "T" as shown in FIGS. 1-3. Exterior plate 102 has insignia or logo area 114 for displaying a team logo, advertisement, or any desired display. The embodiment of insignia area 114 shown here is a centrally located oval area. It is to be understood that insignia area 114 may be of any size or shape and may even incorporate the whole of the outer surface of exterior plate 102. For instance, exterior plate 102 may be comprised of a material having a team color. Exterior plate 102 has two top horizontally oriented tabs 402 and one bottom vertically oriented tab 404. These tabs matingly engage raised slots in a similar configuration on outer pivot leg 104. It is to be understood that exterior plate 102 may have any configuration such as rectangular, oval, letter(s), or even be in the shape of a team mascot. The shape of exterior plate 102 is guided by the type of display it is to exhibit and the desired amount of increased lateral support it will offer ankle brace 100. Removable exterior plate 102 has a material, thickness, configuration, and attachment means providing a desired increase in lateral support to ankle support 100, if any, and a desired display area 114, if any.

The foregoing detailed description is given primarily for clearness of understanding and no unnecessary limitations are to be understood therefore for modifications will become obvious to those skilled in the art upon reading this disclosure and may be made without departing from the spirit of the invention or the scope of the claims.

I claim:

1. An ankle brace with a removable plate comprising:
    a stirrup having a bottom portion and an inner and outer upright leg extending upward therefrom, said inner and said outer upright legs each having an upper pivot portion;
    an inner pivot leg having a lower pivot portion and an upwardly extending support portion, said lower pivot portion being pivotally attached to said upper pivot portion of said inner upright leg extending from said stirrup;
    an outer pivot leg having a lower pivot portion and an upwardly extending support portion, said lower pivot portion being pivotally attached to said upper pivot portion of said outer upright leg extending from of said stirrup; and
    an exterior plate removeably attached to an outer side of said outer pivot leg and having a firm structure extending a substantial height of said support portion of said outer pivot leg.

2. The ankle brace of claim 1 wherein said plate has a logo displayed thereon.

3. The ankle brace of claim 1 wherein said plate has a plurality of tabs extending from a peripheral surface and said outer pivot leg has slots on said upwardly extending support portion positioned to receive said tabs.

4. The ankle brace of claim 1 wherein at least one strap removeably fastens around said upwardly extending support portions of said inner and outer pivot legs under said plate.

5. The ankle brace of claim 1 wherein at least one strap removeably fastens around said upwardly extending support portions of said inner and outer pivot legs over said plate.

6. The ankle brace of claim 1 wherein said plate is configured in the shape of a logo.

7. The ankle brace of claim 1 wherein said inner and outer pivot legs have a pad on an inner surface thereof.

8. An ankle brace comprised of a lower stirrup with a base and an inner and outer upright leg appending upward therefrom, an inner pivot leg having a lower pivot portion and an upwardly extending support portion wherein said lower pivot portion is pivotally connected to an upper pivot portion of said inner upright leg, an outer pivot leg having a lower pivot portion and an upwardly extending support portion wherein said lower pivot portion is pivotally connected to an upper pivot portion of said outer upright leg, and an outer plate having a firm structure removeably connected to an outside surface of said upwardly extending support portion of said outer pivot leg.

9. The ankle brace of claim 8 wherein said plate has an insignia displayed thereon.

10. The ankle brace of claim 8 wherein said plate has a consistency, configuration, and attachment means providing a desired increase in lateral support.

11. The ankle brace of claim 8 wherein said inner and outer pivot legs have at least one retaining strap removeably secured there around and under said plate.

12. The ankle brace of claim 8 wherein said inner and outer pivot legs have at least one retaining strap removeably secured there around and over said plate.

13. The ankle brace of claim 8 wherein said outer surface of said outer pivot leg has a plurality of raised slots in said upwardly extending support portion and said plate has a plurality of tabs extending from a peripheral surface, said slots and said tabs having a matingly configuration.

14. The ankle brace of claim 8 wherein said outer surface of said outer pivot leg has a plurality of male or female snap pieces extending outward from said upwardly extending support portion and said exterior plate has a plurality of the other of said male or female snap pieces extending from an inner surface, said male and said female snap pieces having a matingly configuration.

* * * * *